(12) United States Patent
Partridge et al.

(10) Patent No.: US 8,348,825 B2
(45) Date of Patent: Jan. 8, 2013

(54) EXPANDING MULTI-LUMEN APPLICATOR OPERATING WITHIN A BALLOON

(75) Inventors: Andy Partridge, West Sussex (GB); Ralph Bodenburg, Bochum (DE); E. Ishmael Parsai, Ottawa Hills, OH (US); John J. Feldmeier, Monroe, MI (US)

(73) Assignees: Varian Medical Systems UK Limited, West Sussex (GB); Varian Medical Systems Haan GmbH, Haan (DE)

( * ) Notice: Subject to any disclaimer, the term of this patent is extended or adjusted under 35 U.S.C. 154(b) by 491 days.

(21) Appl. No.: 12/495,234

(22) Filed: Jun. 30, 2009

(65) Prior Publication Data

US 2010/0331601 A1    Dec. 30, 2010

(51) Int. Cl.
*A61N 5/00* (2006.01)

(52) U.S. Cl. .................................... 600/6; 600/3

(58) Field of Classification Search .............. 600/6, 3
See application file for complete search history.

(56) References Cited

U.S. PATENT DOCUMENTS

| | | |
|---|---|---|
| 5,653,683 A | 8/1997 | D'Andrea |
| 5,913,813 A | 6/1999 | Williams et al. |
| 5,931,774 A | 8/1999 | Williams et al. |
| 6,022,308 A | 2/2000 | Williams et al. |
| 6,083,148 A | 7/2000 | Williams et al. |
| 6,413,204 B1 | 7/2002 | Winkler et al. |
| 6,482,142 B1 | 11/2002 | Winkler et al. |
| 6,607,477 B1 * | 8/2003 | Longton et al. .............. 600/3 |
| 7,357,770 B1 | 4/2008 | Cutrer et al. |
| 7,465,268 B2 | 12/2008 | Lubock et al. |
| 7,497,819 B2 | 3/2009 | White et al. |
| 7,497,820 B2 | 3/2009 | White et al. |
| 7,601,113 B2 | 10/2009 | Lebovic et al. |
| 7,662,082 B2 | 2/2010 | White et al. |
| 2003/0163017 A1 * | 8/2003 | Tam et al. ................... 600/3 |
| 2003/0166990 A1 * | 9/2003 | Trauthen et al. ............. 600/3 |
| 2003/0208096 A1 * | 11/2003 | Tam et al. ................... 600/3 |
| 2006/0100475 A1 | 5/2006 | White et al. |
| 2006/0116546 A1 * | 6/2006 | Eng ............................ 600/3 |

(Continued)

FOREIGN PATENT DOCUMENTS

EP    1681077 A1    7/2006

(Continued)

OTHER PUBLICATIONS

About MammoSite, MammoSite 5-Day Targeted Radiation Therapy simplifies radiation therapy, [retrieved on Jan. 14, 2010], retrieved from MammoSite Website, http://www.mammosite.com/physicians/radiation-therapy/about-mammosite.cfm, pp. 1-2.

(Continued)

*Primary Examiner* — Charles A Marmor, II
*Assistant Examiner* — Sunita Reddy
(74) *Attorney, Agent, or Firm* — Houst Consulting

(57) ABSTRACT

A brachytherapy apparatus includes a distal support member and a proximal support member movable relative to the distal support member. The apparatus includes a plurality of elongate treatment members having distal first locations coupled to the distal support member, proximal second locations coupled to the proximal support member, and pathways between the proximal second locations and the distal first locations adapted to receive one or more radiation sources. Each of the treatment members is movable between a generally straight configuration and a curvilinear configuration. An expandable member encloses and provides a spatial volume for the plurality of the treatment members and is adjustable between a contracted configuration and an expanded configuration.

22 Claims, 4 Drawing Sheets

U.S. PATENT DOCUMENTS

| | | | |
|---|---|---|---|
| 2009/0156882 A1 | 6/2009 | Chi et al. | |
| 2009/0264696 A1 | 10/2009 | White et al. | |
| 2010/0048978 A1* | 2/2010 | Sing et al. | 600/6 |
| 2010/0121129 A1 | 5/2010 | White et al. | |
| 2010/0130807 A1 | 5/2010 | White et al. | |
| 2010/0152519 A1 | 6/2010 | White et al. | |
| 2010/0222628 A1 | 9/2010 | White et al. | |

FOREIGN PATENT DOCUMENTS

| | | |
|---|---|---|
| WO | 9815315 A1 | 4/1998 |
| WO | 9962598 A | 12/1999 |
| WO | 2007079278 A1 | 7/2007 |
| WO | 2008112223 A1 | 9/2008 |
| WO | 2008124149 A1 | 10/2008 |

OTHER PUBLICATIONS

APBI—Accelerated Partial Breast Irradiation, [retrieved on Jan. 14, 2010], retrieved from SenoRx Website, http://www.senorx.com/Products/apbi/index.asp, p. 1.

The Most Flexible 5-Day Breast Brachytherapy System, [retrieved on Jan. 14, 2010], retrieved from Cianna Medical Website, http://www.ciannamedical.com/, p. 1.

Ashpole et al., "A New Technique of Brachytherapy for Malignant Gliomas with Caesium-137: A New Method for Utilizing a Remote Afterloading System," Clinical Oncology 2:333-337 (1990).

Abstracts of the 11th Int'l Conf. on Brain Tumor Research and Therapy, Oct. 31-Nov. 3, 1995, Silverado Country Club and Resort, Napa, Cal., Journal of Neuro-Oncology 28: 31-113, 1996 ("Hirschberg").

Johanesen et al., "Intracavity Fractionated Balloon Brachytherapy in Glioblastoma," Acta Neurochir (Vienna, Austria) 141:127-133 (1999).

Friedman and Lewis, "Irradiation of Carcinoma of the Bladder by a Central Intracavitary Radium or Cobalt 60 Source (The Walter Reed Technique)," The American Journal of Roentgenology 79:6-31 (1958).

The Netherlands Patent Office, Search Report, Oct. 18, 2010, 9 pages.

* cited by examiner

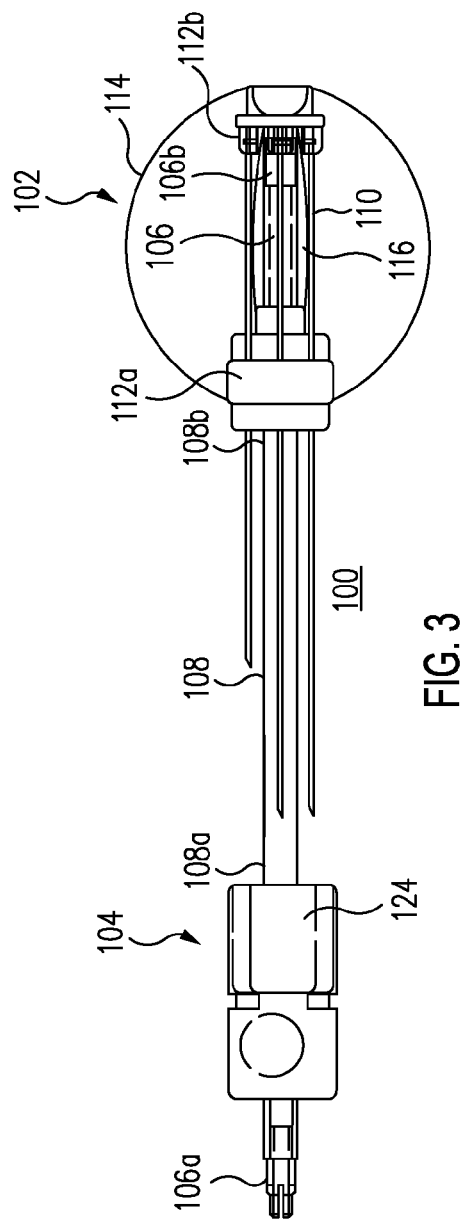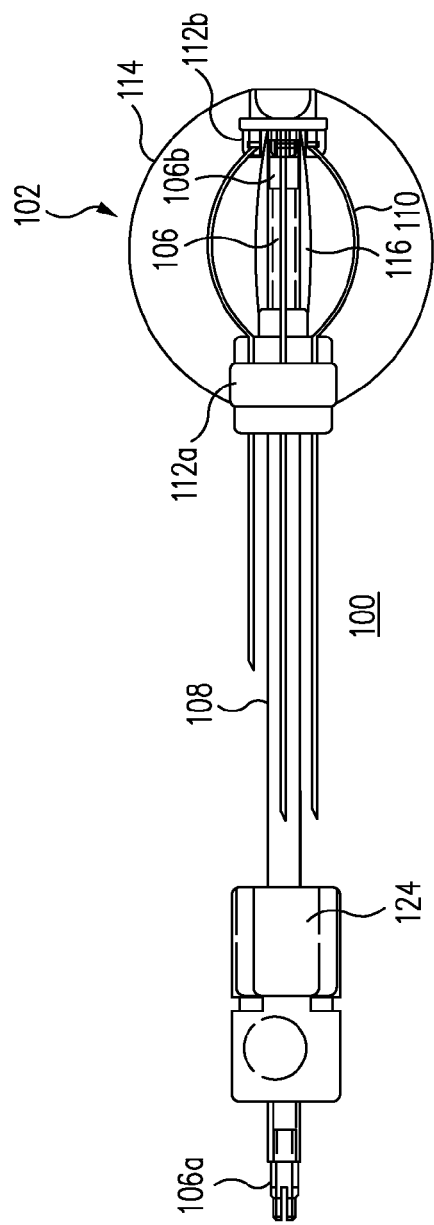

EXPANDING MULTI-LUMEN APPLICATOR OPERATING WITHIN A BALLOON

BACKGROUND

This invention relates in general to radiation therapy and in particular to apparatuses and methods for providing brachytherapy to a human or other mammalian body.

Brachytherapy is a type of radiation therapy that involves placing radioactive materials directly into or immediately adjacent to a target, which may be a tumor or tissue surrounding a cavity that contains cancerous cells. Brachytherapy has been used in treatment of a large number of malignancies including cancer in the uterus, uterine cervix, vagina, prostate, rectum, lung, and breast. One major advantage of brachytherapy is that very high doses of radiation can be delivered locally to the target in a relatively short time, while relatively low doses are delivered in the surrounding tissue. This adheres to the premise in radiation therapy that tumoricidal doses must be deposited in the tumor while sparing as much normal tissue and/or critical organs as possible. The use of brachytherapy in cancer treatment is increasing, partly due to the increasing desire for organ preservation and acceptable cosmetic results.

Significant achievements in brachytherapy have been made, however challenges remain. For example, conventional brachytherapy techniques generally lack the ability to adjust the pathways of radioactive materials in a target site, resulting in less desirable treatment dosimetry. Another issue with conventional brachytherapy techniques is that they require structures often made of metal or plastic for passing radioactive materials right next to the body tissue. The bare metal structures may cause unpleasant effect on patients, prohibits CT/MR scanning of the anatomy to be treated because of excessive artifacts, and create non-uniform dose distributions or overexposure of doses to adjacent healthy tissue.

SUMMARY

The present invention provides brachytherapy apparatuses and methods that are particularly useful in treatment of diseases in the uterus, uterine cervix, vagina, endometrial, rectum, breast, or other body portions. In one embodiment, a brachytherapy apparatus includes a distal support member and a proximal support member movable relative to the distal support member. The apparatus includes a plurality of elongate treatment members having distal ends coupled to the distal support member, proximal ends coupled to the proximal support member, and pathways between the proximal ends and the distal ends adapted to receive one or more radiation sources. Each of the treatment members is movable between a generally straight configuration and a curvilinear configuration. An expandable member encloses the plurality of the treatment members and is adjustable between a contracted configuration and an expanded configuration.

The expandable member may be configured to provide various expanded configurations. In some embodiments, the expanded configuration may be in a generally cylindrical shape. In some embodiments, the expanded configuration may be in a generally spherical shape.

The expandable member may be constructed with a material comprising a polymer selected from the group consisting of polyurethane (PUR), polyvinyl chloride (PVC), low-density polyethylene (LDPE), polyamide, and polyethylene terephthalate (PET). In a preferred embodiment, the expandable member in the contracted configuration has a thickness ranging from 15 to 30 micrometers.

The apparatus may include 2-20 elongate treatment members. Collectively, the treatment members in the curvilinear configuration may provide a generally "egg beater" or "rugby" configuration.

The apparatus may include a first elongate body and a second elongate body that are movable relative to each other. The second elongate body may be slidably or rotatably disposed around the first elongate body and axially movable relative to the first elongate body. The distal and proximal support members may be coupled to the distal portions of the first and second elongate bodies respectively, and move with the first and second elongate bodies.

The apparatus may include a handle portion adapted to operate the treatment members between a generally linear configuration and a curvilinear configuration. The handle portion may be detachable from the apparatus to reduce the profile of the apparatus, or re-attachable to the apparatus for readjustment. The handle may include a scale with reference that indicates the degree of the movement of the treatment members. The handle may further include a lock and release mechanism to limit the movement of the treatment members.

In some embodiments, the apparatus may include a seal member to seal the moving parts from the inflation fluid used for expanding the expandable member.

In some embodiments, the apparatus may further include an extension member outside the expandable member and having a pathway adapted to receive one or more radiation sources. The extension member may be a cervical sleeve configured to be deployed in the uterine cervix. The extension member may also be an intrauterine tandem having a curvature configured to be deployed in the uterus.

In a preferred embodiment, a brachytherapy apparatus includes a first elongate body, a second elongate body, and a plurality of elongate treatment members disposed near the distal portions of the first and second elongate bodies. The second elongate body may be slidably or rotatably disposed around the first elongate body and axially movable relative to the first elongate body. The treatment members may be movable between a generally straight configuration and a curvilinear configuration, and have pathways adapted to receive one or more radiation sources. The plurality of the treatment members are enclosed within an expandable member which may be adjustable between a contracted configuration and an expanded configuration. The apparatus may further include an elongate extension member disposed outside the expandable member and coupled to the distal portion of the first elongate body. The extension member may have a pathway adapted to receive one or more radiation sources. The extension member may be a cervical sleeve to fit in the uterine cervix for treatment of cervical diseases, or a curved intrauterine tandem to be positioned in the uterus for treatment of endometrial diseases.

In a further preferred embodiment, a brachytherapy apparatus includes one or more treatment members each having a distal end coupled to a distal support member, a proximal end coupled to a proximal support member, and a pathway between the distal end and the proximal end adapted to receive one or more radiation sources. An expandable member encloses the one or more treatment members, and changeable between a contracted configuration and an expanded configuration. The expandable member in the contracted configuration may have a thickness ranging from 15 to 30 micrometers. The expandable member is preferably constructed with an elastic polymeric material. The one or more treatment members are preferably movable between a generally straight configuration and curvilinear configuration.

BRIEF DESCRIPTION OF THE DRAWINGS

These and various other features and advantages will become better understood upon reading of the following detailed description in conjunction with the accompanying drawings and the appended claims provided below, where:

FIG. 3 is a side view of an exemplary brachytherapy apparatus showing a plurality of treatment members in a generally straight configuration and an expandable member in an expanded configuration;

FIG. 4 is a side view of an exemplary brachytherapy apparatus showing a plurality of treatment members in a curvilinear configuration and an expandable member in an expanded configuration;

DETAILED DESCRIPTION OF VARIOUS EMBODIMENTS

Figure 1:
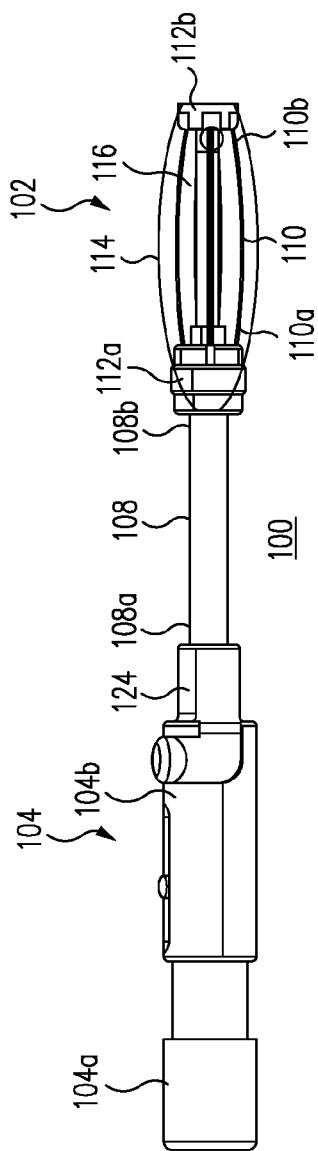
FIG. 1 is a side view of an exemplary brachytherapy apparatus showing a plurality of treatment members in a generally straight configuration and an expandable member in a contracted configuration.

Various embodiments of apparatuses and methods for radiation therapy and imaging are described. It is to be understood that the invention is not limited to the particular embodiments described as such may, of course, vary. An aspect described in conjunction with a particular embodiment is not necessarily limited to that embodiment and can be practiced in any other embodiments. It is also to be understood that the terminology used herein is for the purpose of describing particular embodiments only, and is not intended to be limiting since the scope of the invention will be limited only by the appended claims, along with the full scope of equivalents to which such claims are entitled.

In addition, various embodiments are described with reference to the figures. It should be noted that the figures are not drawn to scale, and are only intended to facilitate the description of specific embodiments. They are not intended as an exhaustive description or as a limitation on the scope of the invention.

All technical and scientific terms used herein have the same meaning as commonly understood by one of ordinary skill in the art to which this invention belongs, unless defined otherwise. As used in the description and appended claims, the singular forms of "a," "an," and "the" include plural references unless the context clearly dictates otherwise. Thus, for example, reference to "a radiation source" includes one or more radiation sources, and reference to "the treatment member" includes one or more treatment members of the form or configuration described herein.

The invention provides a brachytherapy apparatus that can be inserted into a living body and be held in place for delivery of radiation to a target. The apparatus is provided in a form that is as small as possible to aid insertion into the living body. The apparatus has a mechanism to expand once in place in the living body to localize the apparatus, or to provide a space for adjusting treatment members having channels or pathways that are adapted to receive radiation sources. Once in place, the apparatus is connected to a system that provides radiation sources.

As used herein "treatment target" or "target" refers to any portion of a human or mammalian body that is identified to benefit from radiation therapy. The treatment target may include a tumor itself, or tissue surrounding or adjacent to a cavity that contains cancerous cells. The cavity may be a natural void in a living body such as uterus, vagina, uterine cervix, and rectum etc., or created by removing a tumor from the body such as a lumpectomy cavity in the breast.

As used herein "radiation source" refers to any therapeutic element that is operable to deliver a dose of radiation. The radiation source may be a high dose rate radioactive material, medium dose rate radioactive material, low dose rate radioactive material, or any combination. By way of example, suitable radiation sources include Ir-192, Co-60, Cs-131, I-125, Pd-103, Au-198, W-187, Yb-169, Gd-153, Sm-145, Cs-137, Cd-109, Zn-65, Co-58, Co-57, Co-56 and so on. The radiation source maybe in the form of solid or liquid. For example, the radiation source may be contained in a solution, or suspended in a suspension as small particles of solid radionuclides. In some embodiments, the radiation source may be in any suitable solid forms such as cylinders, capsules, plates, lines, and points, etc. The radiation source can be either preloaded into the apparatus at the time of manufacturing, or loaded into the apparatus after it has been deployed in the living body using e.g. an elongate wire carrying the radiation source.

As used herein a "proximal" end or portion of a member, body, or any component refers to the end or portion that is closer to a user along a longitudinal axis of the member, body or component, while a "distal" end or portion refers to the end or portion that is farther to the user. A proximal or distal end includes an extremity and a portion proximal to the extremity.

Figure 2:
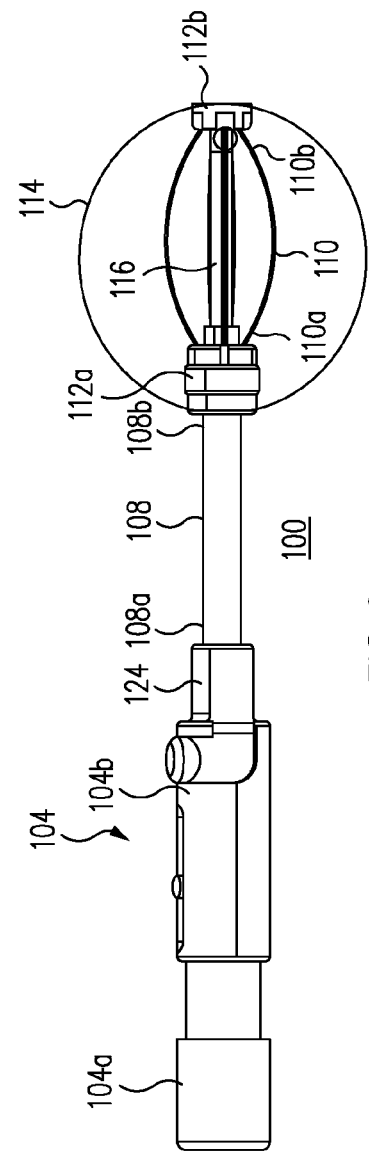
FIG. 2 is a side view of an exemplary brachytherapy apparatus showing a plurality of treatment members in a curvilinear configuration and an expandable member in an expanded configuration.

FIGS. 1-4 illustrate exemplary brachytherapy apparatuses 100 in accordance with some embodiments. In general, the brachytherapy apparatus 100 includes an applicator or treatment delivery portion 102, and a handle portion 104 for operating the treatment delivery portion 102. The treatment delivery portion 102 may be deployed in a target site within a patient's body, e.g., in a void such as vagina, uterus, uterine cervix, rectum, or a lumpectomy cavity in a breast. The handle portion 104 extends from the treatment delivery portion 102 and protrudes outside of the patient's body. The handle portion 104 may be detached from the treatment delivery portion 102 after the apparatus 100 is properly deployed at the target site. The handle portion 104 may be reattached to the treatment delivery portion 102 for readjustment of the apparatus 100 during treatment, or for removing the apparatus 100 out of the patient's body after treatment. The configuration of the treatment delivery portion 102 may be changeable or adjustable between a contracted or collapsed configuration (FIG. 1) and an expanded configuration (FIGS. 2, 3, and 4). A contracted configuration facilitates passage of the apparatus into the target site. An expanded configuration facilitates localizing the apparatus in the target site, providing space for radiation source pathway adjustment, or providing spacing between the radiation source and adjacent critical organs or healthy tissue to prevent overexposure of radiation doses.

The apparatus 100 may include an inner tube or a first elongate body 106 having a proximal portion 106a and a distal portion 106b (FIG. 3 or 4), and an outer shaft or a second elongate body 108 having a proximal portion 108a and a distal portion 108b. The second elongate body 108 may be slidably or rotatably disposed around the first elongate body 106 and axially movable relative to the first elongate body 106. The apparatus 100 includes one or more elongate catheters or treatment members 110 adapted to receive one or more radiation sources. The treatment members 110 include proximal ends 110a, distal ends 110b, and channels or pathways between the proximal and distal ends. The proximal ends 110a of the treatment members 110 may be coupled to the distal portion 108b of the second elongate body 108. The distal ends 110b of the treatment members 110 may be coupled to the distal portion 106b of the first elongate body 106. One or more support members may be used to secure the treatment members 110. For example, a proximal support member 112a may be coupled to the distal portion 108b of the second elongate body 108 for securing the proximal ends 110a of the treatment members 110. A distal support member 112b may be coupled to the distal portion 106b of the first elongate body 106 for securing the distal ends 110b of the treatment members 110. The proximal or distal support members 112a, 112b may have a series of openings adapted to receive or secure the distal or proximal ends 110a, 110b of the treatment members 110. The openings may be spaced apart or evenly spaced apart along a circular path. The distal support member 112b may include a plurality of pivot joints 113 to which the plurality of treatment members 110 are coupled to aid spreading of the treatment members 110 to desired curvilinear configuration.

The treatment members 110 may be flexible or changeable between a generally straight configuration and a curvilinear configuration. The change between a straight configuration and a curvilinear configuration can be caused by changing the linear distance between the proximal ends 110a and the distal ends 110b of the treatment members 110. For example, moving the proximal and/or distal support members 112a, 112b can bring the proximal ends 110a and distal ends 110b of the treatment members 110 closer or take the two ends farther away, thereby bowing or straightening the treatment members 110. The movement between the proximal and distal support members 112a, 112b may be provided by displacing the first and second elongate bodies 106, 108. For example, by displacing the second elongate body 108 in a distal direction, or by displacing the first elongate body 106 in a proximal direction, the proximal and distal ends 110a, 110b of the treatment members 110 may be brought closer to each other, thereby bowing the treatment members 110 from a generally straight configuration. Conversely, the treatment members 110 may be straightened from a curvilinear configuration by displacing the second elongate body 108 in a proximal direction, or by displacing the first elongate body 106 in a distal direction. Collectively, the curvilinear treatment members may form an "egg beater" or "rugby" configuration. The size of the formed "egg beater" or "rugby" may be predetermined based on the size or shape of the target site, and can be controlled by the relative movement between the first and second elongate bodies 106, 108.

The channels or pathways of the treatment members 110 are adapted to receive one or more radiation sources. By changing the configuration of the treatment members 110 between a generally straight and a curvilinear configuration, the pathways of the radiation source or sources within the target site can be adjusted to provide a controlled dosimetry. The number of the treatment members 110 may be chosen depending on the location or size of the target site and may vary widely e.g. ranging from 1 to 20. In some embodiments, 2-20 treatment members 110 are provided. In some embodiments, 2-12 or 4-8 treatment members 110 are provided. The plurality of treatment members and their curvilinear configurations can advantageously aid in delivery of radiation to a target in a three-dimensional way.

In some embodiments, the proximal ends 110a of the treatment members 110 may be extended through the proximal support member 112a and outside of the living body (FIGS. 3 and 4) to be connected to e.g. an after-loader. The treatment members 110 may be continuous members, or be formed from multiple sections connected to each other by suitable means such as bonding or lapping etc.

Expandable member 114 encloses the treatment members 110 and may be bonded or otherwise affixed to the proximal and distal support member 112a, 112b. Expandable member 114 may provide a continuous enclosure for the treatment members 110. The expandable member 114 may be changeable or adjustable between a contracted configuration and an expanded configuration, and as a result, the spatial volume defined by the expandable member 114 is also adjustable. For instance, the expandable member 114 may be in a contracted configuration to facilitate insertion of the apparatus 100 into a target site in a patient's body. Once the apparatus 100 is in place, the expandable member 114 may be expanded to an expanded configuration by e.g. introducing an inflation fluid into the enclosure defined the expandable member 114. The expansion of the expandable member 114 provides a geometry that retains the apparatus 100 in the target site during the treatment session. The expansion of the expandable member 114 also provides room for the treatment members 110 to change from a generally straight configuration to a curvilinear configuration for adjusting the pathways of the radiation sources. The expansion may further provide spacing between the radiation sources and adjacent critical organs or healthy tissues. In some embodiments, the expandable member 114 may be made sufficiently firm to force the target tissue to take the configuration of the expandable member 114 such that the adjacent or surrounding tissue receives a uniform radiation dose.

The expandable member 114 can be configured to form any suitable expanded configurations based on the form or size of the target site in which the apparatus would be deployed. By way of example, for treatment of vaginal diseases, the expandable member 114 can be configured to form an expanded configuration in a generally cylindrical shape or other suitable shapes. For treatment of endometrial diseases, the expandable member 114 can be configured to form an expanded configuration in a generally spherical shape that is suitable to be retained in the uterus. In general, the expandable member 114 can be configured to form an expanded configuration in any regular or irregular shape for deploying in any part of the living body including e.g. lumpectomy cavities in the breast which often have an irregular shape. The size of the expanded configuration can also be predetermined to fit in the target site. In general, the expanded configuration of the expandable member 114 may have a transverse dimension ranging from 1 to 15 cm, or from 2 to 10 cm. By way of example, for treatment of vagina or other diseases, an expanded cylindrical configuration may have a diameter ranging from 2 to 10 cm, and a length ranging from 4 to 10 cm.

For treatment of endometrial or other diseases, an expanded spherical configuration may have a diameter ranging from to 2 to 10 cm.

Various expandable members may be used including inflatable balloons. Inflatable balloons are distensible devices which may be, but not necessarily, constructed with elastic materials. The expandable members 114 may be constructed with materials that are generally impermeable to body fluids such as blood and the like, or impermeable to radiation materials. An impermeable expandable member may be useful in preventing radiation materials or inflation fluid from leaking from the apparatus or preventing contamination of the apparatus or tissue of the patient.

In some preferred embodiments, the expandable member 114 may be constructed with an elastic polymer material. Suitable elastic polymer materials include but are not limited to polyurethane (PUR), polyvinyl chloride (PVC), low-density polyethylene (LDPE), polyamide, polyethylene terephthalate (PET), and the like. By way of example, a balloon may be blow molded from e.g. a pre-extruded polyurethane tubing using "hot blow molding," in which a raw tube is axially stretched, pressurized, and expanded into the inner shape of the molding tool. The raw tube is then exposed to heat, and subsequently chilled. By applying axial and radial stretch on the raw tube, the polymer's chains gain orientation (parallel alignment to stretch vectors), providing the resulting balloon with an extremely thin-walled structure with high tear strength. In some embodiments, the wall thickness of the balloon may range from 10 to 100 micrometers, and preferably from 15 to 30 micrometers. The balloon may be bonded to the proximal and distal support members 112a, 112b using any suitable means such as solvent bonding, heat bonding, ultrasound welding, clamping, etc. In use, as the balloon is inflated, it unfolds to the molded shape. When the balloon is fully filled with an inflation fluid, the balloon may exceed the molded dimensions by a certain percentage under increasing filling pressure until the maximal chain orientation is reached, then rests in a more or less non-compliant phase, not showing dimensional increase over pressure.

Any suitable inflation fluid may be used to expand or inflate the expandable member. The inflation fluid is typically inert. Exemplary inflation fluids include a liquid such as water, saline, mineral oil, or other liquids, or a gas such as air, nitrogen, carbon dioxide or other inert gases. In some embodiments, the inflation fluid may contain media that enhance the contrast of imaging by X-ray or other imaging modality. Contrast enhanced media may include positive contrast media that absorb radiation more strongly than the tissue or structure being imaged, or a negative contrast media, less strongly. The contrast enhanced media can be iodine-based or gadolinium-based. Suitable iodine-based contrast enhanced media include but are not limited to Visopaque (iodixanal, GE Healthcare), omnipaque (iohexol, GE Healthcare), Ultravist (iopromide, Berlex), or isovue (iopamidol, Bracco Diagnostics). Suitable gadolinium-based contrast media include MultiHance (gadobenate dimeglumine, Bracco Diagnostics), Omniscan (GE Healthcare), or Magnevist (Berlex Laboratories).

The inflation fluid may be introduced into the spatial volume enclosed by the expandable member 114 using e.g. a catheter (not shown), which may be supported by the proximal support member 112a. The distal end of the catheter may have an opening in communication with the spatial volume enclosed by the expandable member 114. The proximal end of the catheter may be connected to a source supplying an inflation fluid. The lumen extending from the proximal end to the distal end introduces the inflation fluid into the spatial volume defined by the expandable member 114. A valve may be coupled to the proximal end of the catheter to control the flow of the inflation fluid.

A seal member 116 may be coupled to the distal portions 106b, 108b of the first and second elongate bodies 106, 108 to seal the moving parts and prevent the inflation fluid inside the expandable member 114 from leaking into the gaps between the moving parts of the first and second elongate bodies 106, 108. The seal member 116 may be an elastic balloon bonded to the distal and proximal support members 112a, 112b. Other forms of seals such as O-rings or the like may also be used.

Figure 5:
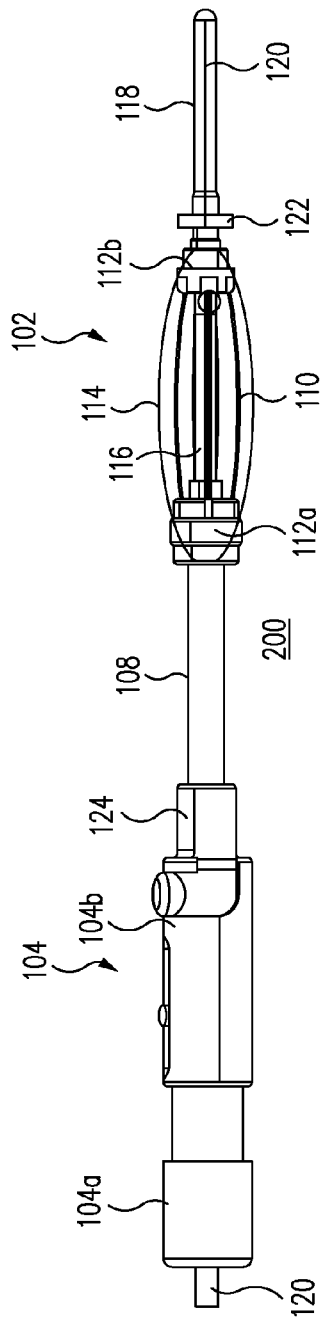
FIG. 5 is a side view of an exemplary brachytherapy apparatus showing a plurality of treatment members enclosed in an expandable member in a contracted configuration, and an extension member.
Figure 6:
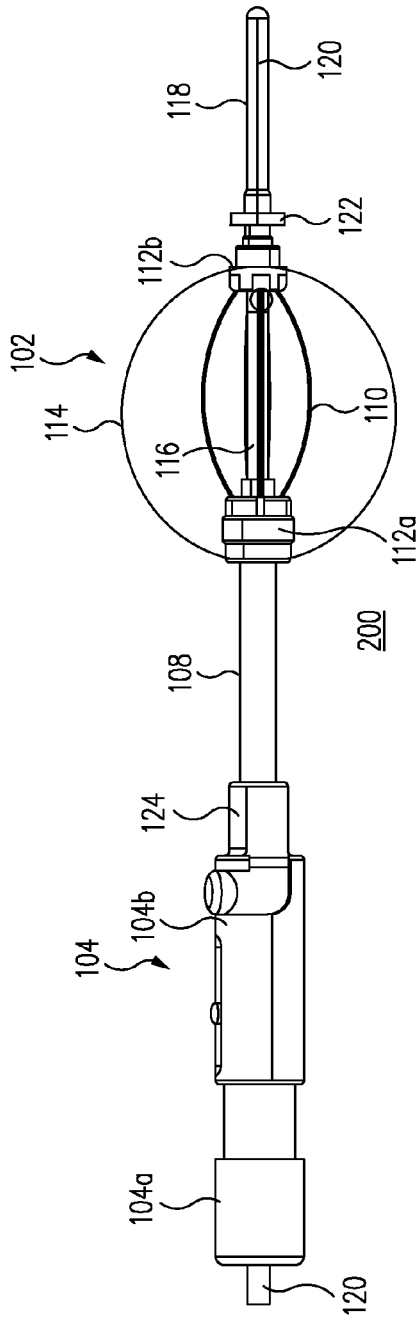
FIG. 6 is a side view of an exemplary brachytherapy apparatus showing a plurality of treatment members enclosed in an expandable member in an expanded configuration, and an extension member.

FIGS. 5-6 illustrate exemplary brachytherapy apparatus 200 in accordance with further embodiments. The apparatus 200 is similar in many aspects to the apparatus 100 described in connection with FIGS. 1-4. For example, the apparatus 200 may include a treatment delivery portion 102 and a handle portion 104. The treatment delivery portion 102 may include a plurality of treatment members 110 and an expandable member 114 enclosing the plurality of treatment members 110. The treatment members 110 may include proximal ends 110a coupled to a proximal support member 112a, distal ends 110b coupled to a distal support member 112b, and pathways between the distal and proximal ends 110a, 110b for receiving one or more radiation sources. Any suitable means can be used to move the proximal support member 112a or the distal support member 112b relative to each other. For example, the distal support member 112b may be coupled to a first elongate body 106, the proximal support member 112a may be coupled to a second elongate body 108 which may be slidably or rotatably disposed around the first elongate body 106. A relative movement or displacement between the first and second elongate bodies 106, 108 in axial direction brings the proximal ends 110a and the distal ends 110b of the treatment members 110 closer or carry the two ends farther away, causing the treatment members 110 to change between a generally straight configuration and a curvilinear configuration. The expandable member 114 may be contracted or expanded using an inflation fluid. A seal member 116 may be coupled to the proximal and distal support members 112a, 112b to provide sealing between the moving parts and the inflation fluid.

The apparatus 200 may further include an extension or attachment member 118 outside the expandable member 114. The extension member 118 may have various lengths, curvatures, or take various angles for deployment in voids of different size or configuration in the living body. The extension member 118 may have a channel adapted to receive one or more radiation sources. Alternatively, the channel in the extension member 118 may be configured for receiving a second treatment member 120 which has a pathway for receiving a radiation source. For example, the second treatment member 120 may be extended from the first elongate body 106 which may have a provided lumen extending from its proximal portion to its distal portion. The distal support member 112b may have a provided opening to allow the second treatment member 120 to extend through into the channel of the extension member 118.

Be way of example, the extension member 118 may be a cervical sleeve that can fit in the uterine cervix for treatment of cervical disease. The cervical sleeve may have a rounded end portion to facilitate smooth insertion into the uterine cervix. The cervical sleeve may have a length that fits in the uterine cervix or through the cervix into the uterus. The cervical sleeve may be coupled to the distal support member 112b by any suitable means such as a connector 122. The connector 122 may have a provided opening to allow e.g. a wire carrying a radiation source passing through, or a second treatment member 120 passing through into the extension member 118. The connector 122 may have a greater cross-section so that it stops in front of the uterine cervix as the sleeve fits in the cervix.

The extension member 118 may also be an intrauterine tandem with varied curvatures to be positioned in the uterus. The intrauterine tandem may be coupled to the distal support member 112b by e.g. a connector 122. The connector 122 may have a provided opening to allow a wire carrying a radiation source or a second treatment member 120 passing through into the intrauterine tandem.

Figure 7:
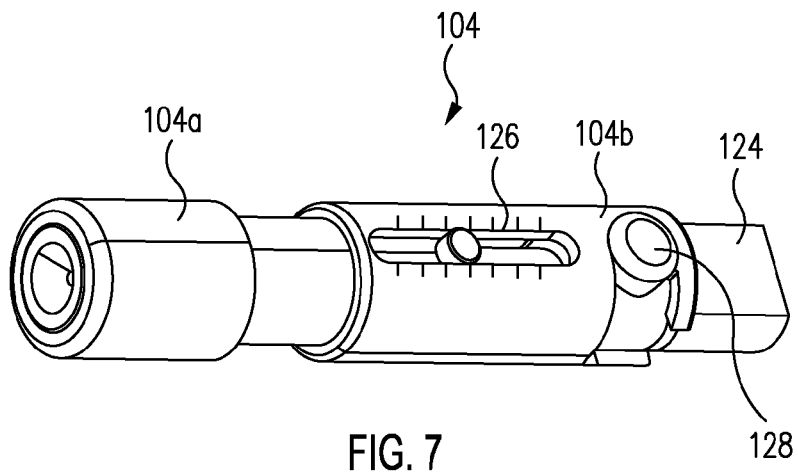
FIG. 7 is a perspective view of an exemplary handle.
Figure 8:
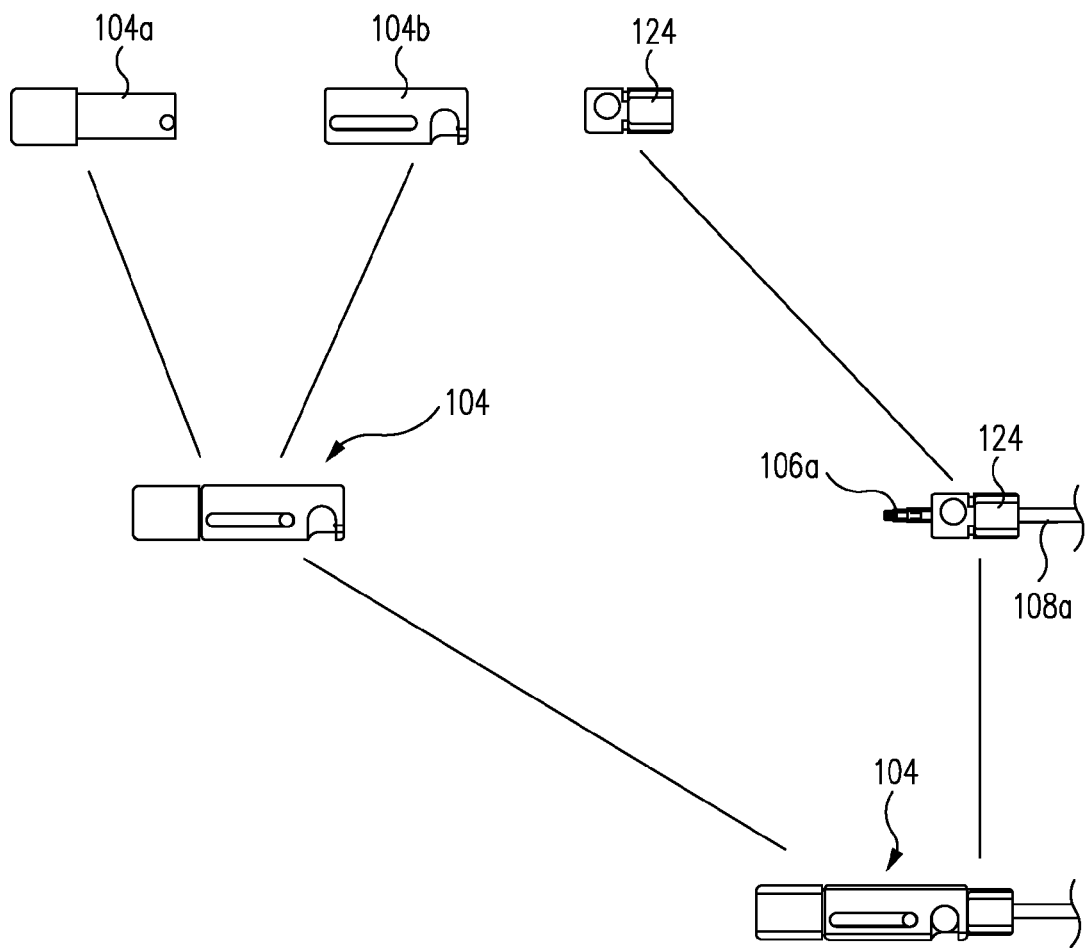
FIG. 8 is an exploded view of the handle illustrated in FIG. 7.

FIGS. 7 and 8 illustrate an exemplary handle portion 104 in accordance with some embodiments. The handle portion 104 may be removably coupled to the treatment delivery portion 102. The handle 104 may include a proximal part 104a and a distal part 104b. The distal part 104b may be a tubular member coupled to the second elongate body 108 via a support member 124 which may be secured to the proximal portion 108a of the second elongate body 108. The proximal part 104a of the handle 104 may be coupled to the first elongate body 106 by any suitable means such as slots, pins, or other mating features on the proximal portion 106a of the first elongate body 106 and the proximal part 104a of the handle 104. The proximal part 104 of the handle 104 may be inserted into the distal part 104b. The proximal part 104a and the distal part 104b may be slidably movable relative to each other in proximal or distal directions.

The distal part 104b of the handle 104 may be provided with a scale 126 that includes reference such as consecutive numbers or letters to indicate the degree of relative movement between the distal part 104b and the proximal part 104a. The reference can be an indicator of the extent of expansion of the treatment members 110. For example, a reference "0" on the scale 126 may indicate no bowing of the treatment members 110 and the treatment members 110 are in generally straight configuration. A reference "10" on the scale 126 may indicate the maximal bowing of the treatment members 110 and the treatment members 110 are in the maximal curvilinear configuration. Any reference between "0" and "10" may indicate a configuration that is in between the generally straight and the maximal curvilinear configuration. This would be beneficial to users in controlling the pathways of the radiation sources and thus the dosimetry to the target.

The handle 104 may include a lock/release mechanism 128 to limit the movement of the first and the second elongate bodies 106, 108. For example, the lock/release mechanism 128 may include a spring-loaded pin that may drop into and come up from a slot on the first elongate body 106. In use, the user may press the button 128 so that the proximal part 104a or distal part 104b of the handle 104 can be moved in a proximal or distal direction, thus displacing the first and the second elongate bodies 106, 108. Once the treatment members 110 are in a desired curvilinear configuration, the user may release the button 128 to lock the first and second elongate bodies 106, 108. The handle 104 can then be detached to reduce the profile of the apparatus 100 or 200. The handle 104 may be reusable and able to be sterilized. FIG. 8 illustrates an exploded view of the handle 104 showing the proximal part 104a, distal part 104b, and a handle support 124 to be coupled to the second elongate body 108.

Prior to the apparatus 100 or 200 being inserted into the living body, the living body would be imaged for diagnostic and treatment selection purposes. Once selected, the apparatus would be inserted and the living body would then be imaged again for the purposes of treatment planning. Various imaging techniques may be used including computed tomography (CT), single photon emission computed tomography (SPECT), magnetic resonance imaging (MRI), magnetic resonance spectroscopy (MRS), and positron emission tomography (PET) etc. The volume enclosed by the expandable member 114 can be filled with a liquid comprising a media that enhances the contrast of imaging. The pathways of the treatment members 110 may also be filled with a media that enhances the contrast of imaging to facilitate reconstruction of images during the treatment planning process.

The brachytherapy apparatus 100 or 200 may be supplied as a kit with unassembled treatment delivery portion 102 and handle portion 104. In use, the handle portion 104 would be attached to the treatment delivery portion 102. The expandable member 114 would initially be in a contracted configuration. While being configured in this small form, the treatment delivery portion 102 is inserted into the living body to the intended target site.

Once in place inside the living body, the expandable member 114 is expanded with an inflation liquid via e.g. a catheter with a provided lumen in communication with the spatial volume enclosed by the expandable member. The expansion of the expandable member 114 can be determined by the amount of the inflation fluid entered into the spatial volume. A valve or other suitable means can be coupled to the catheter to control the flow of the inflation fluid. The relationship between the geometry of the expandable member 114 and the volume of the inflation fluid would be known and reproducible.

Once the expandable member 114 is filled and the valve shut, the expandable member 114 would retain its geometry for the duration of the treatment session. The handle 104 would then be used to adjust the treatment members 110 from a generally straight configuration to a curvilinear configuration, collectively forming to an "egg beater" or "rugby" like configuration. This may be achieved by pressing and holding the button 128 on the handle 104 and move e.g. the distal part 104b of the handle 104 forward. This action would bring the two ends of the treatment members 110 closer inside the expandable member 114 and cause the treatment members 110 to bow or expand.

Once the desired expansion of the treatment members 110 has been reached, the button 128 can be released by removing the pressure, and the position would be retained by a locking mechanism including e.g. pins and slots etc. The relationship between the moving of the handle 104 in axial directions and the radial expansion of the treatment members 110 would be known, and repeatable. The scale 126 on the handle 104 would provide an indication of the degree of expansion of the treatment members 110.

Once the apparatus 100 or 200 is retained, the handle 104 can be detached without changing the expanded configuration of the expandable member 114 or the treatment members 110. The handle 104 can be reattached to the treatment delivery portion 102 to make adjustments if desired. The final configuration and relationship between the expandable member 114 and the treatment members 110 can be derived using instructions for use by referencing the volume of inflation fluid inside the expandable member 114 and the expansion value of the treatment members 110.

The apparatus 100 or 200 can be used to treat cancer in any location within the living body including, but not limited to, cervical, vaginal, endometrial, rectal, and breast diseases. The apparatus 100 or 200 can be customized to have slightly different configurations to accommodate different living body locations. For example, to treat cervical disease, a cervical sleeve 118 of proper length and angle may be coupled to the treatment delivery portion 102 (FIGS. 5-6). A central or second treatment member 120 may be extended past the distal end of the expandable member 114 to enter into the sleeve. In use, the cervical sleeve portion 118 would be inserted into the uterine cervix, and the expandable member 114 portion would be retained in the vagina. The expandable member 114 is then inflated, the treatment members 110 expanded in a manner as described above. For treatment of endometrial or breast diseases, the treatment delivery portion 102 may be inserted into the uterus or into a lumpectomy cavity in the breast, and an extension member 118 would not be required.

Exemplary embodiments of a brachytherapy apparatus and method have been described. The brachytherapy apparatus advantageously uses an expandable member to provide a spatial volume for treatment members which may change between a generally straight and a curvilinear configuration. The use of an expandable member eliminates the need for additional packaging which would otherwise be necessary for filling the void in the target site. The expandable member may have an expanded configuration that distances critical organs such as the bladder, rectum etc. or other healthy tissue away from the radiation source. Comfort to patients will be greatly improved as compared to conventional apparatuses which use heavier metal parts in direct contact with the patient's tissue. Treatment planning will also be improved. A plurality of treatment members may be provided so that the radiation dose would not be centralized but would be more flexible to adjust. This allows sparing critical organs adjacent to the target. Better dose distribution or more flexible dose distribution can be achieved with the use of the expandable member in the target site.

Those skilled in the art will appreciate that various modifications may be made within the spirit and scope of the invention. All these or other variations and modifications are contemplated by the inventors and within the scope of the invention.

What is claimed is:

1. An apparatus for brachytherapy comprising:
   a distal support member;
   a proximal support member movable relative to the distal support member;
   a plurality of elongate treatment members having distal first locations coupled to the distal support member, proximal second locations coupled to the proximal support member, and pathways between the proximal second locations and the distal first locations adapted to receive one or more radiation sources therealong, each of said treatment members being movable between a generally straight configuration and a curvilinear configuration;
   an expandable member enclosing the plurality of the treatment members, the distal support member, and the proximal support member, the expandable member being-inflatable by an inflation medium from a contracted configuration to an expanded configuration, wherein the distal support member and the proximal support member are movable in the expanded configuration to adjust the plurality of elongate treatment members between the generally straight configuration and the curvilinear configuration;
   a catheter configured to introduce the inflation medium to inflate the expandable member to provide the expanded configuration;
   a first elongate body having a distal portion and a proximal portion, a second elongate body having a distal portion and a proximal portion, the second elongate body being disposed around and axially movable relative to the first elongate body, wherein the distal support member is coupled to the distal portion of the first elongate body, and the proximal support member is coupled to the distal portion of the second elongate body; and
   a seal member coupled to the distal portions of the first and second elongate bodies within the expandable member such that the seal member provides sealing that prevents the inflation medium from leaking into moving parts of the first and second elongate bodies.

2. The apparatus of claim 1 wherein the expandable member is configured to provide an expanded configuration in a generally cylindrical shape.

3. The apparatus of claim 2 wherein the expanded configuration in the generally cylindrical shape has a transverse dimension ranging from 2 to 10 cm.

4. The apparatus of claim 1 wherein the expandable member is configured to provide an expanded configuration in a generally spherical shape.

5. The apparatus of claim 4 wherein the expandable member in the generally spherical shape has a transverse dimension ranging from 2 to 10 cm.

6. The apparatus of claim 1 wherein the expandable member is constructed with a material comprising a polymer selected from the group consisting of polyurethane (PUR), polyvinyl chloride (PVC), low-density polyethylene (LDPE), polyamide, and polyethylene terephthalate (PET).

7. The apparatus of claim 1 wherein the expandable member in the contracted configuration has a thickness ranging from 15 to 30 micrometers.

8. The apparatus of claim 1 which comprises 2-20 elongate treatment members.

9. The apparatus of claim 1 wherein the plurality of the treatment members in the curvilinear configuration collectively provide a generally "egg beater" configuration.

10. The apparatus of claim 1 further comprising a handle portion coupled to the proximal portions of the first and second elongate bodies, the handle portion being adapted to axially move the first and second elongate bodies relative to each other.

11. The apparatus of claim 10 wherein the handle portion is removably coupled to the proximal portions of the first and second elongate bodies.

12. The apparatus of claim 11 wherein the handle comprises a scale including reference that indicates the degree of the movement of the treatment members.

13. The apparatus of claim 11 further comprising a lock and release mechanism to limit the movement of the treatment members.

14. The apparatus of claim 1 further comprising an extension member outside the expandable member and coupled to the distal support member, the extension member having a pathway adapted to receive one or more radiation sources.

15. The apparatus of claim 14 wherein the extension member is configured to be deployed in the vagina cervix.

16. The apparatus of claim 14 wherein the extension member has a curvature and is configured to be deployed in the uterus.

17. An apparatus for brachytherapy comprising:
    a first elongate body having a distal portion and a proximal portion;
    a second elongate body having a distal portion and a proximal portion, the second elongate body being disposed around and axially movable relative to the first elongate body;
    a plurality of elongate treatment members having distal first locations coupled to the distal portion of the first elongate body, proximal second locations coupled to the distal portion of the second elongate body, and pathways between the proximal second locations and the distal first locations adapted to receive one or more radiation sources therealong, each of the treatment members being movable between a generally straight configuration and a curvilinear configuration;

an expandable member enclosing the plurality of the treatment members, the distal portion of the first elongate body, and the distal portion of the second elongate body, the expandable member being inflatable by an inflation medium from a contracted configuration to an expanded configuration, wherein the distal portions of the first and the second elongate bodies are movable in the expanded configuration to adjust the plurality of elongate treatment members between the generally straight configuration and the curvilinear configuration;

a catheter configured to introduce the inflation medium to inflate the expandable member to provide the expanded configuration;

an elongate extension member extending outside the expandable member and coupled to the distal portion of the first elongate body, the extension member having a pathway adapted to receive one or more radiation sources therealong; and a seal member coupled to the distal portions of the first and second elongate bodies within the expandable member such that the seal member provides sealing that prevents the inflation medium from leaking into moving parts of the first and second elongate bodies.

18. The apparatus of claim 17 further comprising a second treatment member extended through the first elongate body and into the pathway of the extension member, the second treatment member having a pathway adapted to receive one or more radiation sources therealong.

19. The apparatus of claim 18 wherein the extension member comprises a cervical sleeve to be fit in the uterine cervix for treatment of cervical diseases.

20. The apparatus of claim 18 wherein the extension member comprises a curved intrauterine tandem to be positioned in the uterus for treatment of endometrial diseases.

21. An apparatus for brachytherapy comprising:
a proximal support member;
a distal support member;
one or more treatment members each having a distal first location coupled to the distal support member, a proximal second location coupled to the proximal support member, and a pathway between the distal first location and the proximal second location adapted to receive one or more radiation sources therealong;

an expandable member enclosing the one or more treatment members, the proximal support member and the distal support member, the expandable member being inflatable by an inflation medium from a contracted configuration to an expanded configuration wherein the distal support member and the proximal support member are movable in the expanded configuration to adjust the one or more treatment members between the generally straight configuration and the curvilinear configuration, and having a thickness ranging from 15 to 30 micrometers in the contracted configuration, wherein the one or more treatment members are spaced apart from the expandable member at least in the expanded configuration;

a catheter configured to introduce the inflation medium to inflate the expandable member to provide the expanded configuration;

a first elongate body having a distal portion and a proximal portion, a second elongate body having a distal portion and a proximal portion, the second elongate body being disposed around and axially movable relative to the first elongate body, wherein the distal support member is coupled to the distal portion of the first elongate body, and the proximal support member is coupled to the distal portion of the second elongate body; and a seal member coupled to the distal portions of the first and second elongate bodies within the expandable member such that the seal member provides sealing that prevents the inflation medium from leaking into moving parts of the first and second elongate bodies.

22. The apparatus of claim 21 wherein the expandable member is constructed with a material comprising a polymer selected from the group consisting of polyurethane (PUR), polyvinyl chloride (PVC), low-density polyethylene (LDPE), polyamide, and polyethylene terephthalate (PET).

* * * * *